United States Patent [19]

Viehe et al.

[11] Patent Number: 4,576,759
[45] Date of Patent: Mar. 18, 1986

[54] POLYSUBSTITUTED DIENES

[75] Inventors: Heinz Viehe, Limal; Nadine S. Mesmaeker, Louvain-la-Neuve; Robert Merènyi, Overijse-Maleizen, all of Belgium

[73] Assignee: SOLVAY & Cie (Societe Anonyme), Brussels, Belgium

[21] Appl. No.: 622,745

[22] Filed: Jun. 20, 1984

[30] Foreign Application Priority Data

Jun. 24, 1983 [BE] Belgium .................. 211063

[51] Int. Cl.[4] .................. C07C 57/03
[52] U.S. Cl. .................. 260/410.9 R; 260/413; 560/147; 560/156; 558/438; 558/449; 558/452
[58] Field of Search .................. 260/410.9 M, 410.9 N, 260/413 K, 465.5 A; 560/147, 156

[56] References Cited

U.S. PATENT DOCUMENTS 3,755,411 8/1973 Henrick et al. .................. 560/147
3,801,608 4/1974 Henrick .................. 260/413 K
3,904,662 9/1975 Henrick et al. .................. 260/413 K

FOREIGN PATENT DOCUMENTS 1062556 10/1964 United Kingdom.

OTHER PUBLICATIONS

Chem. Abstracts, vol. 81 (1974), No. 7, 37181h; Babayan et al.
Chem. Abstracts, vol. 85 (1976), No. 17, 123300k; Kocharyan et al.
Chem. Abstracts, vol. 98 (1983), No. 16, 127142b; JP 57,164,173.

Primary Examiner—Natalie Trousof
Assistant Examiner—John T. Sullivan
Attorney, Agent, or Firm—Spencer & Frank

[57] ABSTRACT

The polysubstituted dienes according to the invention correspond to the general formula:

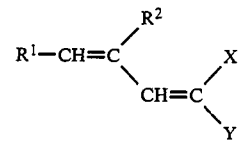

in which:

X denotes a group chosen from the groups SH, $SR^3$, $OR^3$, $SeR^3$, $NHR^3$ and $N=R^3$ in which $R^3$ denotes an aliphatic or cyclic, saturated or unsaturated group containing from 1 to 20 carbon atoms, Y denotes a group chosen from the groups C≡N and

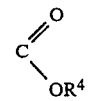

where $R^4$ denotes hydrogen or an aliphatic or cyclic, saturated or unsaturated group containing from 1 to 20 carbon atoms, provided that, when X denotes the group $SCH_3$, Y does not denote the group

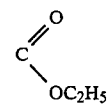

and, when X denotes an $OR^3$ group where $R^3$ is an alkyl group containing at least three carbon atoms, Y does not denote the group C≡N, $R^1$ denotes hydrogen, halogen or an aliphatic, substituted or unsubstituted group containing from 2 to 8 carbon atoms, $R^2$ denotes hydrogen, halogen, an aliphatic, substituted or unsubstituted group containing from 1 to 8 carbon atoms or an aromatic, substituted or unsubstituted group containing from 5 to 8 carbon atoms.

14 Claims, No Drawings

POLYSUBSTITUTED DIENES

The present invention relates to polysubstituted dienes corresponding to the general formula

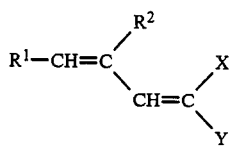

in which:
X denotes a group chosen from the groups SH, $SR^3$, $OR^3$, $SeR^3$, $NHR^3$ and $N=R^3$ in which $R^3$ denotes an aliphatic or cyclic, saturated or unsaturated group containing from 1 to 20 carbon atoms,
Y denotes a group chosen from the groups $C\equiv N$ and

where $R^4$ denotes hydrogen or an aliphatic or cyclic, saturated or unsaturated group containing from 1 to 20 carbon atoms, provided that, when X denotes the group $SCH_3$, Y does not denote the group

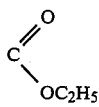

and, when X denotes an $OR^3$ group where $R^3$ is an alkyl group containing at least three carbon atoms, Y does not denote the group $C\equiv N$,
$R^1$ denotes hydrogen, halogen or an aliphatic, substituted or unsubstituted group containing from 2 to 8 carbon atoms,
$R^2$ denotes hydrogen, halogen, an aliphatic, substituted or unsubstituted group containing from 1 to 8 carbon atoms or an aromatic, substituted or unsubstituted group containing from 5 to 8 carbon atoms.

Usually, X denotes a group chosen from the groups $SR^3$, $OR^3$ and $NHR^3$. Most frequently $R^3$ denotes a substituted or unsubstituted alkyl group containing from 1 to 6 carbon atoms; preferably, X denotes an $SCH_3$ or $OCH_3$ group. In a particularly preferred manner, X denotes the methoxy group $OCH_3$.

Usually, Y denotes a group chosen from the groups $C\equiv N$ and

where $R^4$ denotes hydrogen or an alkyl, cycloalkyl, alkenyl or cycloalkenyl group, substituted or unsubstituted, and containing up to 12 carbon atoms, or a substituted or unsubstituted phenyl group containing from 6 to 10 carbon atoms, it being understood that the provisions already expressed continue to apply. In a preferred manner, Y denotes a group chosen from the groups $C\equiv N$ and

where $R^4$ denotes hydrogen or a substituted or unsubstituted alkyl group containing from 1 to 3 carbon atoms, or a substituted or unsubstituted phenyl group containing from 6 to 8 carbon atoms. In a particularly preferred manner, Y denotes a group chosen from the groups $C\equiv N$ and

In a most particularly preferred manner, Y denotes the group

Usually $R^1$ denotes hydrogen or an alkyl, alkoxy, alkenyl or alkenyloxy group, substituted or unsubstituted, and containing from 2 to 6 carbon atoms. In a preferred manner, $R^1$ denotes hydrogen or an alkyl or alkenyl group containing from 2 to 4 carbon atoms; in a particularly preferred manner, $R^1$ denotes hydrogen.

Usually $R^2$ denotes hydrogen or an alkyl, alkoxy, alkenyl or alkenyloxy group, substituted or unsubstituted, and containing from 1 to 6 carbon atoms, or a phenyl, phenoxy, phenylalkyl or phenylalkoxy group, substituted or unsubstituted and containing from 5 to 8 carbon atoms. In a preferred manner, $R^2$ denotes hydrogen, a methoxy group, an alkyl group containing from 1 to 3 carbon atoms or a phenyl group containing 6 carbon atoms; in a particularly preferred manner, $R^2$ denotes hydrogen.

The polysubstituted dienes according to the invention may be in the form of various isomers; they may be employed as intermediates in chemical synthesis, as radical-scavengers and as antioxidants.

The preparation of the polysubstituted dienes according to the invention may be carried out in various ways. For example, a phosphorus-containing derivative may be employed as an intermediate. This preparation is particularly recommended when X denotes an $OR^3$ group. A compound of the formula $X-CH_2-Y$ is subjected to a bromination reaction, followed by a rearrangement known as an Arbusov-Michaelis reaction, consisting of a reaction with a trialkyl phosphite:

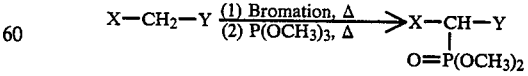

The bromination reaction may be carried out with the use of bromine or N-bromosuccinimide (NBS) for a period of several hours at a temperature in the region of 40° C. The Arbusov-Michaelis reaction is carried out for several hours at a temperature in the region of 80° C. Examples of such a preparation have been described by Dinizo, Friersken, Pobst and Watt (Journal of Organic Chemistry, Volume 41, No. 17, 1976).

In the second stage, the phosphonate compound obtained in this way will lead to the dienes according to the invention via a Wittig-Horner reaction:

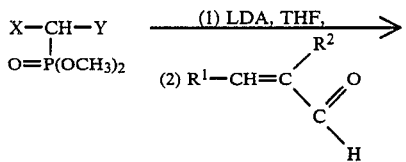

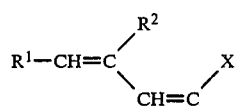

Such a reaction is carried out in an argon atmosphere, with the use of lithium diisopropylamide (LDA) dissolved in tetrahydrofuran (THF). The LDA solution is cooled and the phosphonate

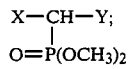

is added slowly; the mixture is then stirred for 35 minutes. The solution is again cooled to −78° C., the temperature at which the aldehyde

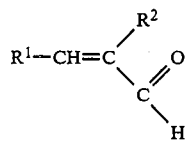

is added.

The temperature is then allowed to rise gradually. After stirring overnight, water is added to the mixture, which is extracted several times with ether, and the ether phases are washed with water saturated with sodium chloride. They are dried over magnesium sulphate and then concentrated before the final product is distilled under reduced pressure.

Another method of preparation applies when X denotes an SR$^3$ group and Y a

group.

This consists in reacting the compound of the formula

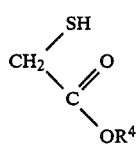

with 3-bromopropyne in the presence of ether and triethylamine, according to the equation

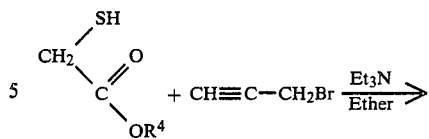

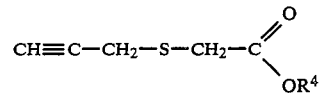

The latter compound is then subjected to a reaction with dimethyl sulphate, under argon, for 3 hours at 75° C. and then to a reaction with a compound NaOR$^3$ in the alcohol R$^3$OH at ambient temperature overnight.

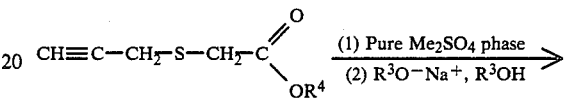

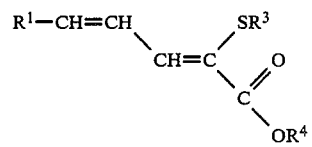

After stirring overnight at ambient temperature, 30 ml of water are added to the solution, which is extracted several times with ether and the ether phases are washed with water saturated with NaCl. The solution is dried over MgSO$_4$ and the filtrate is concentrated.

A third method of preparation applies when X denotes an SR$^3$ group and Y denotes a C≡N group.

The starting point is a mixture composed of a disubstituted allyl bromide of the formula

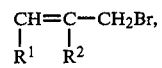

a methylene derivative of the formula

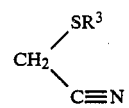

and triethylbenzylammonium chloride (TEBAC), to which a 50% strength aqueous solution of NaOH is added dropwise. After being stirred overnight at room temperature, the mixture is then diluted with water and extracted with ether. The organic phases are then dried over magnesium sulphate MgSO$_4$. After evaporation of the solvent, a fractional distillation makes it possible to obtain the compound corresponding to the formula

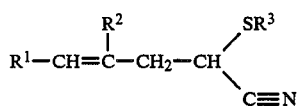

and to remove the starting materials and products of dialkylation. The latter compound is then dissolved in dry dichloromethane. It is added dropwise to a dichloromethane solution of sulphuryl chloride. The mixture thus obtained is stirred until gas has ceased to evolve. The solvent is evaporated off and the product is distilled under reduced pressure. A chlorinated derivative corresponding to the formula $$R^1-CH=C(R^2)-CH_2-C(SR^3)(Cl)(C\equiv N)$$

is then obtained.

This chlorinated derivative is then refluxed in dry dichloromethane in the presence of triethylamine in order to be dehydrochlorinated. After evaporation of the solvent, the residue is treated with dry ether, filtered, and the solvent is evaporated off. The product according to the invention is then obtained by distillation under reduced pressure.

The following examples illustrate the invention.

EXAMPLE 1

Preparation of methyl 2-methoxy-2,4-pentadienoate

The reaction is carried out in an argon atmosphere. $1.1 \times 10^{-2}$ moles of dry diisopropylamine are placed in a flame-dried, three-necked round flask fitted with an argon inlet, a dropping funnel, and a silicone oil trap connected to a tube containing potassium hydroxide. $1.05 \times 10^{-2}$ moles of BuLi dissolved in hexane are added at 0° C. and the cooling bath is removed after five minutes.

After twenty minutes' stirring, the hexane is stripped under a water pump vacuum. Lithium diisopropylamide is thus produced in the form of a white powder which is immediately dissolved in dry THF. This solution is cooled to $-78°$ C.; $10^{-2}$ moles of the phosphonate $$(CH_3O)_2P(=O)-CH(OCH_3)-C(=O)-OCH_3$$

are added to it slowly.

The mixture is stirred for 35 minutes. The solution is again cooled to $-78°$ C., the temperature at which $1.05 \times 10^{-2}$ moles of acrolein $$CH_2=CH-C(=O)H$$

are added. The temperature is allowed to rise gradually. After stirring overnight, water is added to the mixture, which is extracted several times with ether and the ether phases are washed with water saturated with NaCl. The latter are dried over $MgSO_4$ and then concentrated. Methyl 2-methoxy-2,4-pentadienoate is distilled at 60° C. at a pressure of 0.2 mm Hg. A 64% yield is obtained.

The infrared spectrum, measured in dichloromethane, shows absorption bands at 3,080 $cm^{-1}$, 2,840 $cm^{-1}$, 1,720 $cm^{-1}$, 1,625 $cm^{-1}$ and 1,580 $cm^{-1}$.

Mass spectrometry shows ions of masses of 142, 127 and 83 daltons.

The 20-MHz NMR$^{13}$C nuclear magnetic resonance spectra of methyl 2-methoxy-2,4-pentadienoate dissolved in deuterated chloroform confirm that two isomers are obtained in a ratio which may be estimated at 60% of E and 40% of Z. The following characteristics in fact are obtained.

E ISOMER (carbons numbered 1–7)

Z ISOMER (carbons numbered 1'–7')

In the various examples, the carbon atoms are numbered in the order of NMR chemical shift. J is the coupling constant, the value of which is expressed in Hertz. The E isomer and Z isomer are understood to mean the isomers such as defined in the paper by J. E. Blackwood, C. L. Gladys, K. L. Loening, A. E. Petrarca and J. E. Rush (Journal of American Chemical Society, 1968, volume 90, page 509).

| E ISOMER | | | |
|---|---|---|---|
| | δ ppm | mult. | J |
| 1 | 51.5 | Q, s | $^1J = 147.5$ |
| 2 | 55.2 | Q, s | $^1J = 144.7$ |
| 3 | 113.7 | D, m | $^1J = 154$ |
| 4 | 118.8 | DD, d | $^1J_{4-a(b)} = 154.4$ |
| | | | $^1J_{4-b(a)} = 160.2$ |
| | | | $^3J = 5.9$ |
| 5 | 131.4 | D, d | $^1J = 159.3$ |
| 6 | 145.5 | S, m | |
| 7 | 163.0 | S, m | |

| Z ISOMER | | | |
|---|---|---|---|
| | δ ppm | mult. | J |
| 1' | 51.5 | Q, s | $^1J = 147.5$ |
| 2' | 59.9 | Q, s | $^1J = 144.7$ |
| 3' | 125.2 | S, m | $^1J = 161$ |
| 4' | 122.1 | DD, dd | $^1J_{4'-a(b)} = 153.2$ |
| | | | $^2J = 2.5$ |
| | | | $^1J_{4'-b(a)} = 164$ |
| | | | $^2J = 6.7$ |
| 5' | 129.4 | D, s | $^1J = 155.3$ |
| 6' | 145.1 | S, m | |
| 7' | 163.8 | S, m | |

The abbreviation mult. denotes a multiplet.

The UV spectrum in hexane shows a maximum at a wavelength of 263 nm; the extinction coefficient ε equals 15,500.

Finally, elemental analysis gives the following results:

| | | | |
|---|---|---|---|
| Theoretical: | C: 59.14 | H: 7.09 | O: 33.76 |
| Experimental: | C: 59.21 | H: 7.00 | O: 33.79 |

EXAMPLE 2

Preparation of methyl 2,4-dimethoxy-2,4-pentadienoate

The reaction is carried out in an argon atmosphere. $1.1 \times 10^{-2}$ moles of dry diisopropylamine are placed in a flame-dried, three-necked round flask fitted with an argon inlet, a dropping funnel and a silicone oil trap connected to a tube containing potassium hydroxide. $1.05 \times 10^{-2}$ moles of BuLi dissolved in hexane are added at 0° C. and the cooling bath is removed after five minutes.

After twenty minutes, stirring, the hexane is stripped under a water pump vacuum. Lithium diisopropylamide is thus obtained in the form of a white powder which is immediately dissolved in dry THF. This solution is cooled to $-78°$ C.; $10^{-2}$ moles of the phosphonate

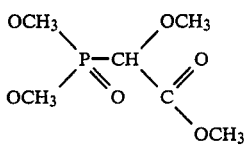

are added to it slowly.

The mixture is stirred for 35 minutes. The solution is again cooled to $-78°$ C., the temperature at which $1.05 \times 10^{-2}$ moles of 2-methoxyacrolein

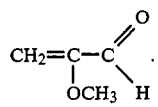

are added. The temperature is allowed to rise gradually. After stirring overnight, water is added to the mixture, which is extracted several times with ether and the ether phases are washed with water saturated with NaCl. The latter are dried over $MgSO_4$ and then concentrated. Methyl 2,4-dimethoxy-2,4-pentadienoate is distilled at 105° C. at a pressure of 12 mm Hg. A yield of over 90% is obtained.

The infrared spectrum, measured in dichloromethane, shows absorption bands at 3,050 $cm^{-1}$, 2,850 $cm^{-1}$, 1,745 $cm^{-1}$, 1,645 $cm^{-1}$ and 1,590 $cm^{-1}$.

Mass spectrometry shows ions of a mass of 172 daltons.

The 20-MHz NMR$^{13}$C nuclear magnetic resonance spectrum of methyl 2,4-dimethoxy-2,4-pentadienoate dissolved in deuterated chloroform gives the following results:

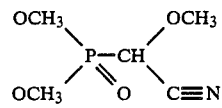

| | δ ppm | mult. | J |
|---|---|---|---|
| 1 | 51.9 | Q, s | $^1J = 147.4$ |
| 2 | 54.4 | Q, s | $^1J = 143.7$ |
| 3 | 59.5 | Q, s | $^1J = 145.4$ |
| 4 | 89.2 | DD, d | $^1J4 - a(b) = 160$ |
| | | | $^1J4 - b(a) = 164.8$ |
| 5 | 119.8 | D, dd | $^1J = 160$ |
| 6 | 145.7 | S, m | |
| 7 | 156.0 | S, m | |
| 8 | 164.3 | S (quint.) | |

UV spectrometry in hexane shows a maximum at a wavelength of 279 nm; $\epsilon = 8,900$.

EXAMPLE 3

Preparation of 2-methoxy-2,4-pentadienenitrile

The reaction is carried out in an argon atmosphere. $1.1 \times 10^{-2}$ moles of dry diisopropylamine are placed in a flame-dried, three-necked round flask fitted with an argon inlet, a dropping funnel and a silicone oil trap connected to a tube containing potassium hydroxide. $1.05 \times 10^{-2}$ moles of BuLi dissolved in hexane are added at 0° C. and the cooling bath is removed after five minutes.

After twenty minutes' stirring, the hexane is stripped under a water pump vacuum. Lithium diisopropylamide is thus obtained in the form of a white powder which is immediately dissolved in dry THF. This solution is cooled to $-78°$ C.; $10^{-2}$ moles of the phosphonate

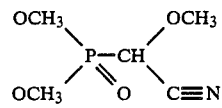

are added to it slowly.

The mixture is stirred for 35 minutes. The solution is again cooled to $-78°$ C., the temperature at which $1.05 \times 10^{-2}$ moles of 2-methoxyacrolein

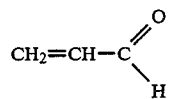

are added. The temperature is allowed to rise gradually. After stirring overnight, water is added to the mixture, which is extracted several times with ether and the ether phases are washed with water saturated with NaCl. The latter are dried over $MgSO_4$, then concentrated and distilled at 70° C. at a pressure of 12 mm Hg. A 70% yield of 2-methoxy-2,4-pentadienenitrile is obtained, as a colourless liquid.

The infrared spectrum, measured in dichloromethane, shows absorption bands at 3,100 $cm^{-1}$, 2,850 $cm^{-1}$, 2,235 $cm^{-1}$ and 2,215 $cm^{-1}$ (C≡N), 1,625 $cm^{-1}$ and 1,595 $cm^{-1}$ (C=C).

Mass spectrometry shows ions of masses of 109 and 94 daltons.

The 50-MHz NMR$^{13}$C nuclear magnetic resonance spectra of 2-methoxy-2,4-pentadienenitrile dissolved in deuterated chloroform confirm that two isomers have been obtained (in a proportion which can be estimated at 75% of E and 25% of Z); the following characteristics are in fact found:

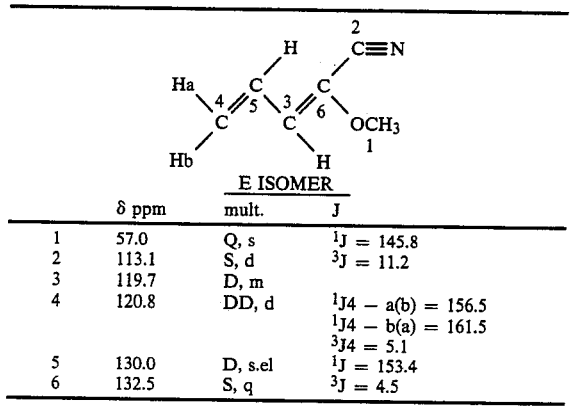

E ISOMER

| δ ppm | mult. | J |
|---|---|---|
| 1 | 57.0 | Q, s | $^1J = 145.8$ |
| 2 | 113.1 | S, d | $^3J = 11.2$ |
| 3 | 119.7 | D, m | |
| 4 | 120.8 | DD, d | $^1J_4 - a(b) = 156.5$ |
|   |       |       | $^1J_4 - b(a) = 161.5$ |
|   |       |       | $^3J_4 = 5.1$ |
| 5 | 130.0 | D, s.el | $^1J = 153.4$ |
| 6 | 132.5 | S, q | $^3J = 4.5$ |

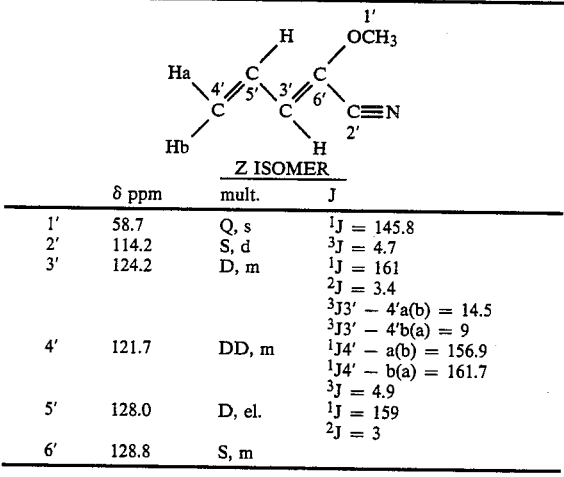

Z ISOMER

| δ ppm | mult. | J |
|---|---|---|
| 1' | 58.7 | Q, s | $^1J = 145.8$ |
| 2' | 114.2 | S, d | $^3J = 4.7$ |
| 3' | 124.2 | D, m | $^1J = 161$ |
|    |       |      | $^2J = 3.4$ |
|    |       |      | $^3J_{3'} - 4'a(b) = 14.5$ |
|    |       |      | $^3J_{3'} - 4'b(a) = 9$ |
| 4' | 121.7 | DD, m | $^1J_{4'} - a(b) = 156.9$ |
|    |       |       | $^1J_{4'} - b(a) = 161.7$ |
|    |       |       | $^3J = 4.9$ |
| 5' | 128.0 | D, el. | $^1J = 159$ |
|    |       |        | $^2J = 3$ |
| 6' | 128.8 | S, m | |

The UV spectrum in hexane shows a maximum at a wavelength of 257 nm; ε=16,500.

Finally, elemental analysis gives the following results:

| | C | H | N |
|---|---|---|---|
| Theoretical: | 66.04 | 6.46 | 12.83 |
| Experimental: | 66.08 | 6.39 | 12.93 |

EXAMPLE 4

Preparation of 2-methylthio-2,4-pentadienenitrile 20 ml of a 50% strength aqueous solution of NaOH are added dropwise to a mixture composed of 6.05 g ($5 \times 10^{-2}$ moles) of allyl bromide, 4.35 g ($5 \times 10^{-2}$ moles) of methylthio acetonitrile and 0.3 g of TEBAC. After being stirred overnight at room temperature, the mixture is diluted with water and extracted with ether.

The organic phases are dried over MgSO4. After evaporation of the solvent, fractional distillation at 104° C. at a pressure of 40 mm of mercury enables 2-methylthio-4-pentenenitrile to be obtained in a yield which varies between 30 and 60%. The infrared spectrum of 2-methylthio-4-pentenenitrile shows absorption bands at 3,100 cm$^{-1}$, 2,850 cm$^{-1}$, 2,250 cm$^{-1}$ and 1,650 cm$^{-1}$; mass spectrometry shows an ion with a mass of 127 daltons.

$2 \times 10^{-2}$ moles of 2-methylthio-4-pentenenitrile are then dissolved in 50 ml of dry CH$_2$Cl$_2$. $2 \times 10^{-2}$ moles of SO$_2$Cl$_2$ dissolved in 10 ml of CH$_2$Cl$_2$ are added dropwise. The mixture is stirred until gas evolution has ceased (silicone oil trap). The solvent is evaporated off and distillation is carried out at 82° C. at a pressure of 12 mm of mercury. 2-Chloro-2-methylthio-4-pentenenitrile is obtained in a yield of over 95%.

Finally, 1.61 g ($10^{-2}$ moles) of 2-chloro-2-methylthio-4-pentenenitrile are refluxed for 20 hours in 30 ml of dry CH$_2$Cl$_2$, in the presence of 2.02 g (2 equivalents) of triethylamine. After evaporation of the solvent, the residue is treated with 4 30 ml portions of dry ether, filtered, and the solvent is evaporated off. The product is distilled at 40° C. at a pressure of 0.05 mm Hg.

2-Methylthio-2,4-pentadienenitrile is obtained in a yield in the region of 90%.

The infrared spectrum, measured in dichloromethane, shows absorption bands at 3,100 cm$^{-1}$, 2,850 cm$^{-1}$, 2,230 cm$^{-1}$, 1,615 cm$^{-1}$ and 1,575 cm$^{-1}$.

Mass spectrometry shows ions with masses of 125 and 110 daltons.

The 20-MHz NMR$^{13}$C nuclear magnetic resonance spectra of 2-methylthio-2,4-pentadienenitrile dissolved in deuterated chloroform confirm that two isomers have been obtained in a ratio which can be estimated at 65% of E and 35% of Z.

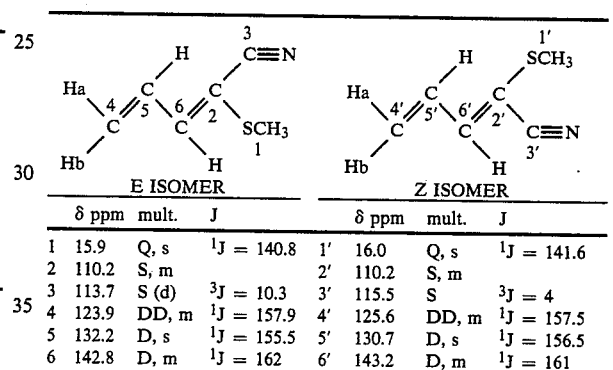

| | E ISOMER | | | | Z ISOMER | | |
|---|---|---|---|---|---|---|---|
| | δ ppm | mult. | J | | δ ppm | mult. | J |
| 1 | 15.9 | Q, s | $^1J = 140.8$ | 1' | 16.0 | Q, s | $^1J = 141.6$ |
| 2 | 110.2 | S, m | | 2' | 110.2 | S, m | |
| 3 | 113.7 | S (d) | $^3J = 10.3$ | 3' | 115.5 | S | $^3J = 4$ |
| 4 | 123.9 | DD, m | $^1J = 157.9$ | 4' | 125.6 | DD, m | $^1J = 157.5$ |
| 5 | 132.2 | D, s | $^1J = 155.5$ | 5' | 130.7 | D, s | $^1J = 156.5$ |
| 6 | 142.8 | D, m | $^1J = 162$ | 6' | 143.2 | D, m | $^1J = 161$ |

EXAMPLE 5

Preparation of methyl 2-methoxy-4-methyl-2,4-pentadienoate

The reaction is carried out in an argon atmosphere. $1.1 \times 10^{-2}$ moles of dry diisopropylamine are placed in a flame-dried, three-necked round flask fitted with an argon inlet, a dropping funnel and a silicone oil trap connected to a tube containing potassium hydroxide. $1.05 \times 10^{-2}$ moles of BuLi dissolved in hexane are added at 0° C. and the cooling bath is removed after five minutes.

After twenty minutes, stirring, the hexane is stripped under a water pump vacuum. Lithium diisopropylamide is thus obtained in the form of a white powder which is immediately dissolved in dry THF. This solution is cooled to −78° C.; $10^{-2}$ moles of the phosphonate

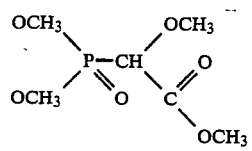

are added to it slowly.

The mixture is stirred for 35 minutes. The solution is again cooled to −78° C., the temperature at which $1.05 \times 10^{-2}$ moles of 2-methylacrolein

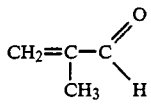

are added. The temperature is allowed to rise gradually. After stirring overnight, water is added to the mixture, which is extracted several times with ether and the ether phases are washed with water saturated with NaCl. The latter are dried over MgSO$_4$ and then concentrated. Methyl 2-methoxy-4-methyl-2,4-pentadienoate is distilled at 45° C. at a pressure of 0.05 mm Hg. A yield of 80% is obtained.

The infrared spectrum, measured in dichloromethane, shows absorption bands at 3,080 cm$^{-1}$, 2,830 cm$^{-1}$, 1,720 cm$^{-1}$, 1,630 cm$^{-1}$ and 1,595 cm$^{-1}$.

Mass spectrometry shows ions with masses of 156, 141 and 97 daltons.

The 20-MHz NMR$^{13}$C nuclear magnetic resonance spectra of methyl 2-methoxy-4-methyl-2,4-pentadienoate dissolved in deuterated chloroform confirms that two isomers have been obtained in a ratio which can be estimated at 75% of E and 25% of Z. The following characteristics are, in fact, obtained:

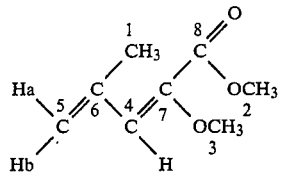

E ISOMER

| | δ ppm | mult. | J |
|---|---|---|---|
| 1 | 20.9 | Q, m | |
| 2 | 50.9 | Q, s | $^1J = 147,5$ |
| 3 | 54.6 | Q, s | $^1J = 144.5$ |
| 4 | 108.2 | D, m | $^1J = 157$ |
| 5 | 114.1 | DD, quint | $^1J5 - a(b) = 156.6$ |
| | | | $^3J = 5.6$ |
| 6 | 138.1 | S, m | |
| 7 | 147.2 | S, m | |
| 8 | 164.0 | S, dq | $^3J = 11$ |

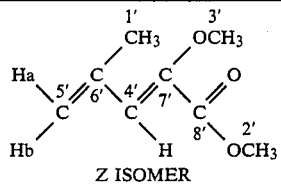

Z ISOMER

| | δ ppm | mult. | H |
|---|---|---|---|
| 1' | 20.5 | Q, m | |
| 2' | 50.9 | Q, s | $^1J = 146$ |
| 3' | 58.9 | Q, s | $^1J = 145.2$ |
| 4' | 125.1 | D, m | $^1J = 158$ |
| 5' | 114.1 | DD, quint | $^1J5' - a(b) = 156.6$ |
| | | | $^3J = 5.6$ |
| 6' | 138.8 | S, m | |
| 7' | 144.1 | S, m | |
| 8' | 163.8 | S, m | |

The UV spectrum in hexane shows a maximum at a wavelength of 273 nm (ε=27,700).

EXAMPLE 6

Preparation of 2-methoxy-4-methyl-2,4-pentadienenitrile

The reaction is carried out in an argon atmosphere. $1.1\times10^{-2}$ moles of dry diisopropylamine are placed in a flame-dried, three-necked round flask fitted with an argon inlet, a dropping funnel and a silicone oil trap connected to a tube containing potassium hydroxide. $1.05\times10^{-2}$ moles of BuLi dissolved in hexane are added at 0° C. and the cooling bath is removed after five minutes.

After twenty minutes' stirring, the hexane is stripped under a water pump vacuum. Lithium diisopropylamide is thus obtained in the form of a white powder which is immediately dissolved in dry THF. This solution is cooled to $-78°$ C.; $10^{-2}$ moles of the phosphonate

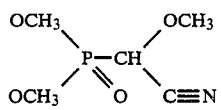

are added to it slowly.

The mixture is stirred for 35 minutes. The solution is again cooled to $-78°$ C., the temperature at which $1.05\times10^{-2}$ moles of 2-methylacrolein

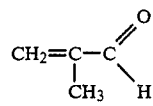

are added. The temperature is allowed to rise gradually. After stirring overnight, water is added to the mixture, which is extracted several times with ether and the ether phases are washed with water saturated with NaCl. They are dried over MgSO$_4$, and then concentrated. Methyl 2-methoxy-2,4-pentadienoate distills at 83° C. at a pressure of 12 mm Hg. An 86% yield of 2-methoxy-4-methyl-2,4-pentadienenitrile is obtained, in the form of a colourless liquid.

The infrared spectrum, measured in dichloromethane, shows absorption bands at 3,100 cm$^{-1}$, 2,850 cm$^{-1}$, 2,230 cm$^{-1}$ and 2,220 cm$^{-1}$, 1,620 cm$^{-1}$ and 1,598 cm$^{-1}$.

Mass spectrometry shows an ion with a mass of 123 daltons.

The 20-MHz NMR$^{13}$C nuclear magnetic resonance spectra of 2-methoxy-4-methyl-2,4-pentadienenitrile dissolved in deuterated chloroform confirm that two isomers have been obtained, in a ratio which can be estimated at 65% of E and 35% of Z. The following characteristics are in fact found:

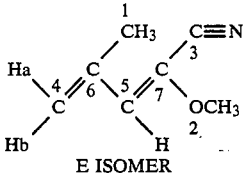

E ISOMER

| | δ ppm | mult. | J |
|---|---|---|---|
| 1 | 20.5 | Q, ddd | $^1J = 127.3$ |
| | | | $^3J1 - 4b = 10.7$ |
| | | | $^3J1 - 4a(b) = 4.3$ |
| | | | $^3J1 - 5(4a) = 6.2$ |
| 2 | 57.0 | Q, s | $(^1J) = 145.5$ |
| 3 | 114.2 | S, d | $^3J = 11.9$ |
| 4 | 120.4 | DD, quint | $^1J = 158.05$ |
| | | | $^3J = 6$ |
| 5 | 122.8 | D, m | $^1J = 154.5$ |
| 6 | 129.2 | S, m | |

-continued

| | | | |
|---|---|---|---|
| 7 | 136.6 | S, q.el. | $^3J = 7$ |

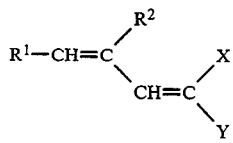

Z ISOMER

| δ ppm | | mult. | J |
|---|---|---|---|
| 1' | 21.8 | Q, m | |
| 2' | 58.6 | Q, s | $^1J = 145.7$ |
| 3' | 114.2 | S, d | |
| 4' | 121.2 | DD, m | |
| 5' | 125.1 | D, m | |
| 6' | 128.1 | S, m | |
| 7' | 138.5 | S, m | |

The UV spectrum in hexane shows a maximum at a wavelength of 260 nm (ε=14,300).

We claim:

1. A polysubstituted diene of the formula:

in which:

X is selected from the group consisting of SH, SR³, OR³, SeR³, NHR³ and N=R³, in which R³ is an aliphatic or cyclic group containing from 1 to 20 carbon atoms;

Y is selected from the group consisting of C≡N and

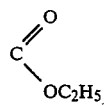

in which R⁴ is hydrogen or an aliphatic or a cyclic group containing form 1 to 20 carbon atoms, provided that, when X is SCH₃, Y is not

when X is SCH₃ and R¹ and R² are H, Y is not

and, when X is OR³ and R³ is an alkyl group containing at least three carbon atoms, Y is not C≡N;

R¹ is selected from the group consisting of hydrogen, halogen and an aliphatic group containing from 2 to 8 carbon atoms; and R² is selected from the group consisting of hydrogen, halogen, an aliphatic group containing from 1 to 8 carbon atoms and an aromatic group containing from 5 to 8 carbon atoms.

2. A diene according to claim 1, wherein X is selected from the group consisting of SR³, OR³ and NHR³; R⁴ is hydrogen, an alkyl, cycloalkyl, alkenyl or cycloalkenyl group containing up to 12 carbon atoms, or a phenyl group containing from 6 to 10 carbon atoms; R¹ is hydrogen or an alkyl, alkoxy, alkenyl or alkenyloxy group containing from 2 to 6 carbon atoms; and R² is hydrogen, an alkyl, alkoxy, alkenyl or alkenyloxy group containing from 1 to 6 carbon atoms, or a phenyl, phenoxy, phenylalkyl or phenylalkoxy group containing from 5 to 8 carbon atoms.

3. A diene according to claim 2, wherein R³ is an alkyl group containing from 1 to 6 carbon atoms.

4. A diene according to claim 1, wherein Y is selected from the group consisting of C≡N and

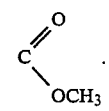

where R⁴ is hydrogen, an alkyl group containing from 1 to 3 carbon atoms, or a phenyl group containing from 6 to 8 carbon atoms.

5. A diene according to claim 1, wherein R¹ is hydrogen or an alkyl or alkenyl group containing from 2 to 4 carbon atoms, and R² is hydrogen, a methoxy group, an alkyl group containing from 1 to 3 carbon atoms, or a phenyl group containing six carbon atoms.

6. A diene according to claim 1, wherein X is selected from the group consisting of OCH₃ and SCH₃.

7. A diene according to claim 1, wherein Y is selected from the group consisting of C≡N and

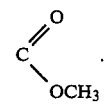

8. A diene according to claim 1, wherein R¹ and R² are hydrogen.

9. A diene according to claim 1, wherein X is OCH₃.

10. A diene according to claim 1, wherein Y is

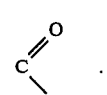

11. A diene according to claim 6, wherein Y is selected from the group consisting of C≡N and

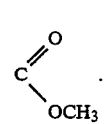

12. A diene according to claim 11, wherein R¹ and R² is hydrogen.

13. A diene according to claim 9, wherein Y is

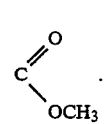

14. A diene according to claim 13, wherein R¹ and R² are hydrogen.

* * * * *